US007470514B2

(12) United States Patent
Ali et al.

(10) Patent No.: US 7,470,514 B2

(45) Date of Patent: Dec. 30, 2008

(54) METHOD OF DIAGNOSING, MONITORING, AND STAGING PROSTATE CANCER

(75) Inventors: Shujath Ali, Santa Clara, CA (US); Susana Salceda, San Jose, CA (US); Yongming Sun, San Jose, CA (US); Robert Cafferkey, Mountain View, CA (US)

(73) Assignee: diaDexus, Inc., South San Francisco, CA (US)

( * ) Notice: Subject to any disclaimer, the term of this patent is extended or adjusted under 35 U.S.C. 154(b) by 417 days.

(21) Appl. No.: 10/939,560

(22) Filed: Sep. 13, 2004

(65) Prior Publication Data

US 2005/0079483 A1 Apr. 14, 2005

Related U.S. Application Data

(62) Division of application No. 09/700,700, filed as application No. PCT/US99/10548 on May 12, 1999, now Pat. No. 6,861,215.

(60) Provisional application No. 60/086,265, filed on May 21, 1998.

(51) Int. Cl.
*C12Q 1/68* (2006.01)

(52) U.S. Cl. ........................ 435/6; 435/91.2; 536/23.1; 536/24.3

(58) Field of Classification Search .................... 435/6, 435/91.2; 536/23.1, 24.3
See application file for complete search history.

(56) References Cited

U.S. PATENT DOCUMENTS 5,506,106 A 4/1996 Croce et al.

FOREIGN PATENT DOCUMENTS

| | | |
|---|---|---|
| WO | WO 98/36054 | 8/1998 |
| WO | WO 99/00498 A1 | 1/1999 |
| WO | WO 00/55174 | 9/2000 |
| WO | WO 00/55174 A1 | 9/2000 |
| WO | WO 01/51633 A2 | 7/2001 |

OTHER PUBLICATIONS

Stanton, P et al, 1994, Br J Cancer, 70: 427-433.*
Iehle, C et al, 1999, J Steroid Biochem Mol Biol, 68: 189-195.*
Abbaszadegan, M R, et al, 1994, Cancer Res, 54: 4676-4679.*
Kibel, AS et al, 2000, J urol, 164(1): 192-6.*
Dong et al, 2000, Cancer Research, 60: 3880-3883.*
Zhau, HE, 1994, J Cell Biochem, Suppl 19: 208-216.*
Ren, C et al, 1998, Cancer Res, 58(6): 1285-90.*
Gingrich, JR et al, 1996, Cancer res, 56(18): 4096-4102.*
Russo, V et al, 1995, Int J Cancer, 64: 216-221.*
Yerushalmi et al (Gene, 2001, vol. 265, pp. 55-60).*
Caillou et al (Journal of Clinical Endocrinology and Metabolism, 2001, vol. 86, pp. 3351-3358).*
EMBL Accession No. AA525010 Jul. 19, 1997.

Blok et al., "Isolation of cDNAs That Are Differentially Expressed Between Androgen-Dependent and Androgen-Independent Prostate Carcinoma Cells Using Differential Display PCT", The Prostate 1995 26:213-224.

Chang et al., "Differentially Expressed Genes in Androgen-dependent and -independent Prostate Carcinomas", Cancer Research 1997 57:4075-4081.

Friedrich et al., "Differentiation-Stage Specific Expression of Oncoprotein 18 in Human and Rat Prostatic Adenocarcinoma", The Prostate 1995 27:102-109.

Hooper et al., "Testisin, a New Human Serine Proteinase Expressed by Premeiotic Testicular Germ Cells and Lost in Testicular Germ Cell Tumors", Cancer Research 1999 59:3199-3205.

Inoue et al., "Cloning and Tissue Distribution of a Novel Serine Protease esp-1 from Human Eosinophils", Biochemical and Biophysical Research Communications 1998 252:307-312.

Deguchi, T et al. Detection of Micrometastatic Prostate Cancer Cells in the Bone Marrow of Patients with Prostate Cancer, British Journal of Cancer, 1997, vol. 75, No. 5, pp. 634-638.

An, G. et al. Cloning of Prostate-Specific Genes that are Suppressed In Metastatic Prostate Cancer by a PCR Southern Differential Hybridization Method, Proc. Am. Assoc. Can. Res., vol. 39, p. 208.

Abate-Shen et al., "*Nkx3.1*; Pten Mutant Mice Develop Invasive Prostate Adenocarcinoma and Lymph Node Metastases[1]", Cancer Research 2003 63(14):3886-3890.

Bierberich et al., "Prostate-specific and Androgen-dependent Expression of a Novel Homeobox Gene", J. Biol. Chem. 1996 271(50):31779-31782 reprinted as pp. 1-10.

He et al., "A Novel Human Prostate-Specific, Androgen-Regulated Homeobox Gene (NKX3.1) That Maps to 8p21, a Region Frequently Deleted in Prostate Cancer", Genomics 1997 43:69-77.

Herbrand et al., "Transcription factors *Nkx3.1* and *Nkx3.2* (*Bapx1*) play an overlapping role in sclerotomal development of the mouse", Mechanisms of Development 2002 117:217-224.

Kim et al., "*Nkx3.1* Mutant Mice Recapitulate Early Stages of Prostate Carcinogenesis[1]", Cancer Research 2002 62:2999-3004.

Kim et al., "Cooperativity of *Nkx3.1* and *Pten* loss of function in a mouse model of prostate carcinogenesis", Proc. Natl. Acad. Sci. USA 2002 99(5):2884-2889 reprinted as pp. 1-10.

Prescott et al., "Isolation and Androgen Regulation of the Human Homeobox cDNA, NKX3.1", The Prostate 1998 35:71-80.

Sciavolino et al., "Tissue-Specific Expression of Murine *Nkx3.1* in the Male Urogenital System", Developmental Dynamics 1997 209:127-138.

NCBI Genbank Accession U80669 [gi:1732377] Dec. 10, 1996-Jun. 3, 1999 with Revision History.

(Continued)

*Primary Examiner*—Larry R. Helms
*Assistant Examiner*—Minh-Tam Davis
(74) *Attorney, Agent, or Firm*—Licata & Tyrrell P.C.; Keith R. McCollum

(57) ABSTRACT

The present invention provides a new method for detecting, diagnosing, monitoring, staging and prognosticating prostate cancer.

7 Claims, No Drawings

OTHER PUBLICATIONS

He et al., "A Novel Human Prostate-Specific, Androgen-Regulated Homeobox Gene (NKX3.1) That Maps to 8p21, a Region Frequently Deleted in Prostate Cancer", Genomics 1997 43:69-77 XP-002084749.

López-Otín et al., "Breast and Prostate Cancer:An Analysis of Common Epidemiological, Genetic, and Biochemical Features", Endocrine Reviews 1998 19(4):365-396 XP-002220464.

Olsson et al., "Reverse Transcriptase-Polymerase Chain Reaction Assays for Prostate Cancer", Urologic Clinics of North America 1997 24(2):367-377 XP002923009.

Prescott et al., "Isolation and Androgen Regulation of the Human Homeobox cDNA, NKX3.1", The Prostate 1998 35:71-80 XP-002084750.

Voeller et al., "Coding Region of NKX3.1, a Prostate-Specific Homeobox Gene on 8p21, Is Not Mutated in Human Prostate Cancers[1]", Cancer Research 1997 57:4455-4459 XP-002084751.

Database EMBL Human NKX3.1 mRNA, Dec. 17, 1996 Database accession No. HSU80669 XP002084746.

Database EMBL Human NKX3.1 gene, Oct. 15, 2002 Database accession No. NM_006167 XP-002223221.

Deguchi, T et al. Detection of Micrometastatic Prostate Cancer Cells In the Bone Marrow of Patients with Prostate Cancer, British Journal of Cancer, 1997, vol. 75 No. 5, pp. 634-638.

* cited by examiner

SEQUENCE LISTING

<160> NUMBER OF SEQ ID NOS: 7

<210> SEQ ID NO 1
<211> LENGTH: 1936
<212> TYPE: DNA
<213> ORGANISM: Homo sapiens
<220> FEATURE:
<221> NAME/KEY: misc_feature
<222> LOCATION: (106)..(106)
<223> OTHER INFORMATION: n=a, c, g or t
<220> FEATURE:
<221> NAME/KEY: misc_feature
<222> LOCATION: (455)..(455)
<223> OTHER INFORMATION: n=a, c, g or t
<220> FEATURE:
<221> NAME/KEY: misc_feature
<222> LOCATION: (459)..(459)
<223> OTHER INFORMATION: n=a, c, g or t -continued

```
<220> FEATURE:
<221> NAME/KEY: misc_feature
<222> LOCATION: (468)..(468)
<223> OTHER INFORMATION: n=a, c, g or t
<220> FEATURE:
<221> NAME/KEY: misc_feature
<222> LOCATION: (1541)..(1541)
<223> OTHER INFORMATION: n=a, c, g or t
<220> FEATURE:
<221> NAME/KEY: misc_feature
<222> LOCATION: (1908)..(1908)
<223> OTHER INFORMATION: n=a, c, g or t

<400> SEQUENCE: 1

aatggtatgc caacttaagt atttacaggg tggcccaaat agaacaagat gcactcgctg     60

tgattttaag acaagctgta taaacagaac tccactgcaa gagggngggc cgggccagga    120

gaatctccgc ttgtccaaga caggggccta aggagggtct ccacactgct gctaggggct    180

gttgcatttt tttattagta gaaagtggaa aggcctcttc tcaacttttt tcccttgggc    240

tggagaattt agaatcagaa gtttcctgga gttttcaggc tatcatatat actgtatcct    300

gaaaggcaac ataattcttc cttccctcct tttaaaattt tgtgttcctt tttgcagcaa    360

ttactcacta aagggcttca ttttagtcca gatttttagt ctggctgcac ctaacttatg    420

cctcgcttat ttagcccgag atctggtctt ttttntgtnt ttttttntt tccgtctccc    480

caaagcttta tctgtcttga ctttttaaaa aagtttgggg gcagattctg aattgggcta    540

aaagacatgc atttttaaaa ctaggcaact tcttatttct ttcctttaaa aatacatagc    600

attaaatccc aaatcctatt taaagacctg acagcttgag aaggtcacta ctgcatttat    660

aggaccttct ggtggttctg ctgttacgtt tgaagtctga caatccttga gaatctttgc    720

atgcagagga ggtaagaggt attggatttt cacagaggaa gaacacagcg cagaatgaag    780

ggccaggctt actgaggctg tccagtggag ggctcatggg tgggacatgg aaaagaaggc    840

agcctaggcc ctggggagcc cagtccactg agcaagcaag ggactgagtg agccttttgc    900

aggaaaaggc taagaaaaag gaaaaccatt ctaaaacaca acaagaaact gtccaaatgc    960

tttgggaact gtgtttattg cctataatgg gtccccaaaa tgggtaacct agacttcaga   1020

gagaatgagc agagagcaaa ggagaaatct ggctgtcctt ccattttcat tctgttatct   1080

caggtgagct ggtagagggg agacattaga aaaaaatgaa acaacaaaac aattactaat   1140

gaggtacgct gaggcctggg agtctcttga ctccactact taattccgtt tagtgagaaa   1200

cctttcaatt ttcttttatt agaagggcca gcttactgtt ggtggcaaaa ttgccaacat   1260

aagttaatag aaagttggcc aatttcaccc cattttctgt ggtttgggct ccacattgca   1320

atgttcaatg ccacgtgctg ctgacaccga ccggagtact agccagcaca aaaggcaggg   1380

tagcctgaat tgctttctgc tctttacatt tcttttaaaa taagcattta gtgctcagtc   1440

cctactgagt actctttctc tcccctcctc tgaatttaat tctttcaact tgcaatttgc   1500

aaggattaca catttcactg tgatgtatat tgtgttgcag ngaaaagaaa aaagtgtctt   1560

tgtttaaaat tacttggttt gtgaatccat cttgcttttt ccccattgga actagtcatt   1620

aacccatctc tgaactggta gaaaaacatc tgaagagcta gtctatcagc atctgacagg   1680

tgaattggat ggttctcaga accatttcac ccagacagcc tgtttctatc ctgtttaata   1740

aattagtttg ggttctctac atgcataaca aaccctgctc caatctgtca cataaaagtc   1800

tgtgacttga agtttagtca gcacccccac caaactttat ttttctatgt gtttttttgca   1860

acatatgagt gttttgaaaa taaagtaccc atgtctttat taaaaaanaa aaaaaagggc   1920
```

-continued

```
ggccgccgac tagtga                                                  1936


<210> SEQ ID NO 2
<211> LENGTH: 637
<212> TYPE: DNA
<213> ORGANISM: Homo sapiens

<400> SEQUENCE: 2

gtaggggcag acttactgcc ttgaacgaaa gacgatggtc ctcgctcagc ctcactccaa    60

ttatgttcct ctaggtgggg caggtagggg gtccagcttc ctgcttgctg gtggttcagg   120

tcatgcgtcc agccttgtcc cttctgacct gggccctacc cacggggaaa tgttcccata   180

gcagaagaat cagccccaca gtgcaggggt gtgttagtgg ggaacgggct ctgggctcct   240

gtgggaacca gggacccccct atcttggtac cggtcattgg atgtatcccc agctcatgcc   300

tgtgtctgtc ttggcccgtg tggtcaccct gtgttcatct ctctcccagc catggcctct   360

caaactgggg ttttcgtctc cctatgaggg ggtcctggta tgtacgcgtt cggtgggccc   420

gcggtgcatg tctcccggtg cagtgcatgc tggggttccc tggggccctg ggcccctcgt   480

aggatagaca gagcctgtcc taaccttccg gaagtgcatg ctggggaggc cccttgcctg   540

ctgaccttct gtgctcagga cgactaatcg gccacatgac caccactctg tcccatggga   600

ttcctagaga agtctcacta agagcccagc acactca                            637


<210> SEQ ID NO 3
<211> LENGTH: 2693
<212> TYPE: DNA
<213> ORGANISM: Homo sapiens
<220> FEATURE:
<221> NAME/KEY: misc_feature
<222> LOCATION: (586)..(586)
<223> OTHER INFORMATION: n=a, c, g or t
<220> FEATURE:
<221> NAME/KEY: misc_feature
<222> LOCATION: (1480)..(1480)
<223> OTHER INFORMATION: n=a, c, g or t
<220> FEATURE:
<221> NAME/KEY: misc_feature
<222> LOCATION: (1532)..(1532)
<223> OTHER INFORMATION: n=a, c, g or t
<220> FEATURE:
<221> NAME/KEY: misc_feature
<222> LOCATION: (1562)..(1566)
<223> OTHER INFORMATION: n=a, c, g or t
<220> FEATURE:
<221> NAME/KEY: misc_feature
<222> LOCATION: (1569)..(1569)
<223> OTHER INFORMATION: n=a, c, g or t
<220> FEATURE:
<221> NAME/KEY: misc_feature
<222> LOCATION: (1571)..(1571)
<223> OTHER INFORMATION: n=a, c, g or t
<220> FEATURE:
<221> NAME/KEY: misc_feature
<222> LOCATION: (1631)..(1631)
<223> OTHER INFORMATION: n=a, c, g or t
<220> FEATURE:
<221> NAME/KEY: misc_feature
<222> LOCATION: (2266)..(2512)
<223> OTHER INFORMATION: n=a, c, g or t

<400> SEQUENCE: 3

gctcctacag ccgcatctgc gttaacatag catccctatg gccactgtct cccttgatcc    60

ccacagccat cctaggagaa aggcagaatg tcataatttg ctaaaaggga tgctgaggct   120

ctgggaggga aagggacttg cctaaagccc cagggtgaag cagcatctct ggactcccag   180

tccagtgatc ttgcccaata ctttgctgct tgcctatacc cctctaactt ggtcaacagc   240
```

-continued

```
acatcacagg gcaagcccaa tccctgcttc atttttatat atgggcgctg gtccacagcc    300
ccactctcca gccatttgga aacaaaaaca gatgctattg ttcttcctta gagaacgtgg    360
ccagtggaga cggcacactg gaaatcagag tgaatgttct tgaaagaggg tcacgggtca    420
acaaggccca gccaaaggat gcagtagaac cattttcctt agaaatcttt gggagtgaag    480
taggcttcag ccactaccca tccctgccct tgcggctacc actaccccat tagtttagac    540
agggtcgggc ggggaggggt gtggagaaga aatgagcttg cctgtngccc ccaggctccc    600
tctgtcctag ctcaggtctg ggtgccattc tttacactcg tgtgctcgct cacgcacaca    660
tcacacacct tgctggtcac acagtcacag actcgcctct gctcctgtgg tccagtggcc    720
ggacaccccc tgggatggct caaaggagtc aggacttgga agtggggaca tcagggtagc    780
tgaaggaaat ccacacaccc agagcatctc ggagttcaga ctctcagacc tgaagtaggc    840
gcccccggga ctgggctagg agttggacgg aatggaggat ggaggacagc gagaagaaag    900
gaagagaaat gcaaagtgtg ggcagccgcc aagagtgaaa atagagggaa gtgtcatgca    960
agtgctggac agaaggcggc aggtgggacg agccccacag ccccctcctc aaaaacgacc   1020
acctccagga ctcagtgatc cctggggggc aggctctgcc agccctcggc cacacgtggc   1080
tccggcaccc atggtcccag tgccttggat ggagacggcc agttctggcg gccagatgtg   1140
gtgctctgga atccagtccc atttccttcc tggccacgcc tgttccagcg gcctctttgg   1200
ctgcattcag cccctactta cctggggacc ccggctgggg cacaagagca ccaggggggt   1260
agggcccaaa gggatcaggg gaagcctctg gcctggaggg tatggggcac gcttccccaa   1320
gggcggaccc ggcaggagga agcccaggag ctgggtcctg ccgcccagga gctgggccct   1380
gccacccagg ccgggctagg gacatggcag ggcctgggca tcctgacgct ggacttgggc   1440
gacctgggag gcacagggag gggagagatg ggcggccccn acccagcgca gtgccggcca   1500
caccccaagg cggttgccag agcttaaggc cnggccccag caggagaaca tcccagctcc   1560
annnnnccnc nccgcagcca gtgctccttg tcaagctccc cccgtcactc caggtgggag   1620
ccaccccggt naggggggtgt gccacttgcc cccagggcac tcctctgggc atcccgggtg   1680
ggggattttg gggccgtggg gggcagtctc tggtacctgt gtgcgtcagg gatgctctgc   1740
acctgcaacc aggtgtcgtc cacgggcggg ggcatgggca tggtgacagt ggtcctgttg   1800
atgtcaccga tgatgctgag cgcctccttc agcgcgtggt gcatgtgcag catctcgtcg   1860
tgctgctgtg cctgctctgc caactcctcc atcagtgtgt tctggttccc acatgagtac   1920
atattggcca gcggctccga gatgatgaac tccggggtct gagagtgggc aaacagggaa   1980
gaaggttggg acctggtgcc tgtgccgccc tggctgcctt gctgggccct tctgggactg   2040
tgcgctggac ttggagcccc ttggagtatg gcttttcaca cgggcttcta taccgcttcg   2100
actggaagat ccacctcccc actgcctttt ctcactcaga tggggacacc gaggtccaga   2160
ggaaaagaca cctgtcaaat gtcacagatc tgggagggga cttaagacct atcatgccaa   2220
gaggacacct gtctactcag tttttttttg gtggggcggg gggcgnnnnn nnnnnnnnnn   2280
nnnnnnnnnn nnnnnnnnnn nnnnnnnnnn nnnnnnnnnn nnnnnnnnnn nnnnnnnnnn   2340
nnnnnnnnnn nnnnnnnnnn nnnnnnnnnn nnnnnnnnnn nnnnnnnnnn nnnnnnnnnn   2400
nnnnnnnnnn nnnnnnnnnn nnnnnnnnnn nnnnnnnnnn nnnnnnnnnn nnnnnnnnnn   2460
nnnnnnnnnn nnnnnnnnnn nnnnnnnnnn nnnnnnnnnn nnnnnnnnnn nnggagttgg   2520
agttgatgcc tggatacagg agctctgtgg gtgggagtga gacaaaacac agggtcctga   2580
```

-continued

```
gctctgggga ccaagcaatg tcctctggtg aaaaaaatcc tggacttgct ggcagaagat   2640

ttgcctctta cttgccatgt gctctgaata catttacctg ccctctggga aaa          2693


<210> SEQ ID NO 4
<211> LENGTH: 292
<212> TYPE: DNA
<213> ORGANISM: Homo sapiens
<220> FEATURE:
<221> NAME/KEY: misc_feature
<222> LOCATION: (284)..(284)
<223> OTHER INFORMATION: n=a, c, g or t

<400> SEQUENCE: 4

aagaatatga gatttgctta gaaatgaagg actggaagga gcccacagag ttattttta     60

aactatccag taaggcttag agggtttcaa tcagaaatat gtgttagggg aaaaaatgca    120

ctttttctat attaaaaaat attattttct tcttttaaat gtaaagcatt cctattgtga    180

agaattgaga aaatacagaa aagtacaaag aaaaacatta cctacaactc caccatccgt    240

gattatcact gttcacattt gtggctcatt tttcagtatk tctnttattt aa            292


<210> SEQ ID NO 5
<211> LENGTH: 2694
<212> TYPE: DNA
<213> ORGANISM: Homo sapiens
<220> FEATURE:
<221> NAME/KEY: misc_feature
<222> LOCATION: (52)..(52)
<223> OTHER INFORMATION: n=a, c, g or t
<220> FEATURE:
<221> NAME/KEY: misc_feature
<222> LOCATION: (74)..(74)
<223> OTHER INFORMATION: n=a, c, g or t
<220> FEATURE:
<221> NAME/KEY: misc_feature
<222> LOCATION: (76)..(76)
<223> OTHER INFORMATION: n=a, c, g or t
<220> FEATURE:
<221> NAME/KEY: misc_feature
<222> LOCATION: (81)..(81)
<223> OTHER INFORMATION: n=a, c, g or t
<220> FEATURE:
<221> NAME/KEY: misc_feature
<222> LOCATION: (93)..(93)
<223> OTHER INFORMATION: n=a, c, g or t
<220> FEATURE:
<221> NAME/KEY: misc_feature
<222> LOCATION: (98)..(98)
<223> OTHER INFORMATION: n=a, c, g or t
<220> FEATURE:
<221> NAME/KEY: misc_feature
<222> LOCATION: (123)..(123)
<223> OTHER INFORMATION: n=a, c, g or t
<220> FEATURE:
<221> NAME/KEY: misc_feature
<222> LOCATION: (132)..(132)
<223> OTHER INFORMATION: n=a, c, g or t
<220> FEATURE:
<221> NAME/KEY: misc_feature
<222> LOCATION: (173)..(173)
<223> OTHER INFORMATION: n=a, c, g or t
<220> FEATURE:
<221> NAME/KEY: misc_feature
<222> LOCATION: (217)..(217)
<223> OTHER INFORMATION: n=a, c, g or t
<220> FEATURE:
<221> NAME/KEY: misc_feature
<222> LOCATION: (257)..(257)
<223> OTHER INFORMATION: n=a, c, g or t
<220> FEATURE:
<221> NAME/KEY: misc_feature
<222> LOCATION: (2539)..(2539)
<223> OTHER INFORMATION: n=a, c, g or t
```

-continued

<400> SEQUENCE: 5

```
tactatattg ctcagcattt ctaagtattc tctaagtgct ctttatttat gntttaaaat     60
agctctctta cccngntgcg ncgactagaa ganttgntt taggaaacaa tgaaatatat    120
aanttgccag antcaattgg agccctctta catctaaaag atctctggtt ggntggaaat    180
caactgtcag aattacctca ggaaatagga aatctgnaga acctgctgtg tttagatgtc    240
tctgaaaaca ggttggnaag acttcctgaa gaaatcagtg gcctgacttc attaacggat    300
ttagtcattt cccagaactt attagaaacg attccggatg gcattggaaa actaaagaaa    360
ctgtcaatct tgaaggtgga tcagaataga ctcacacagt tgcctgaagc agttggggaa    420
tgtgaaagtc tcactgagtt agttcttaca gaaaatcagc tcctgaccct gcctaaaagc    480
attggaaaac taaagaagtt gagcaacttg aatgcagaca gaaataaatt agtgtcctta    540
ccaaaagaga tcggcgggtg ctgcagcctc actgtgttct gtgtacgtga caacagacta    600
actcggatac ctgcagaggt gtcacaggca acagaacttc atgtcctgga tgtggcaggg    660
aacaggttgc tgcatctacc tttatccctg actgccttga agttgaaggc tctgtggcta    720
tctgacaacc agtcccagcc cctgcttaca ttccagacag acacagacta caccacagga    780
gagaagattt taacctgtgt cttacttcct cagctgcctt ctgaacctac ttgtcaagag    840
aatctgcctc gctgtggtgc actggagaac ttggtaaatg atgtctctga tgaagcctgg    900
aacgagcgtg ctgtcaacag agtcagtgcg atccgatttg tggaggatga gaaagatgaa    960
gaagacaatg agacgagaac acttctaagg cgagccactc cacacccagg ggagttaaag   1020
cacatgaaaa agacagtgga gaatttacgg aatgacatga atgctgctaa aggactggac   1080
tcaaacaaaa acgaggtcaa tcatgccatt gaccgagtga ccacttctgt gtagagtttc   1140
acctccaagt tttacctcct gtgtcttcct ctgctgtcga gacgttcctg tctgcttccc   1200
gggagcctca cgtgctcctt gtcctaacca gcccccgcgc gccatcttcc cgtggagtgt   1260
ggggaagctg ctgtctccca ggaagtgcct tactcatccc gcaaccagtc agcgcaccag   1320
tggtctcccg gtgtgatttt tttttttttt aatttcagtt gtttgtaata agtagaatac   1380
actactgtaa acatacgacc tttgtttttg tcttatgttg gggtaaagga aagcaggaag   1440
gggaattttt atcctcctcc cttccgtaaa gtgctgggat attttgaatc ccccaagttc   1500
ccttggacct actgatgaga gatagtttta tgtatgggga aaaatggata ctttttaaac   1560
ctttttggc agctcagatg gtgtaaattt taaaatttg tataggtatt tcataacaaa   1620
aatatgtatt tcttttttgt tattttatct tgaaaacggt acatatttta gtatttgtgc   1680
agaaaaacaa gtcctaaagt atttgttttt atttgtacca tccacttgtg ccttactgta   1740
tcctgtgtca tgtccaatca gttgtaaaca atggcatctt tgaacagtgt gatgagaata   1800
ggaatgtggt gttttaaagc agtgttgcat tttaatcagt aatctacctg gtggatttgt   1860
ttttaaccaa aaagatgaat tatcaatgat ttgtaattat atcggttgat tttttttgaa   1920
aagatgaacc aaaggatttg actgctaata ttttattcct tacacttttt ttctgaataa   1980
gtctctcata atgagtgcag tgtcagactg tgcctactct gatggtatgt gccatttgta   2040
aaataaaata gagcagaaaa acacaaaaag agaacactgg ttcagacatt cagtgggcaa   2100
gtaaattatg gactgcaaaa taatgatttt tattcaagaa agctttaaaa gttttatatc   2160
cagatataca accacaataa agcaaaataa cctactatca aaatagaaat gttgctatct   2220
ttataagtgc aatttaattt gtaaatagag tttgaatcaa agtatcacaa aatactgctt   2280
```

-continued

```
caagatttaa ttttaaatct gctaatttaa gggatattgg gaaaagtttt ggtgtgtttc   2340

tgttgatttc ttttttgtat gctgtgataa aagagaaatg aaaagtgcca gtcactgtgt   2400

ggtgtctagg aaaatcatat atattttttt ctccaagaaa taaattcatc ctggacattg   2460

gccatacagc tttttaaaat tattactttg tatgttcaag tgatagcagg tagccaaatt   2520

ctttgacagt gtgctctgnt ctgttaaata tctaaattac ccgtcagttg tgagtgacct   2580

cctgtgggac ttgcattcac atggggcaga gcccagaatt gcctttgact ctggctagta   2640

attttgggtt gtggctatct ggccaattgg actccttata aacccgtctt caac         2694
```

```
<210> SEQ ID NO 6
<211> LENGTH: 1335
<212> TYPE: DNA
<213> ORGANISM: Homo sapiens
<220> FEATURE:
<221> NAME/KEY: misc_feature
<222> LOCATION: (17)..(17)
<223> OTHER INFORMATION: n=a, c, g or t

<400> SEQUENCE: 6

tcatatagta ggaaganaag cacctaggtt tgaggccagg gctggctgct gtcagaacct     60

aggccctccc ctgccttgct ccacacctgg tcaggggaga gaggggagga aagccaaggg    120

aagggaccta actgaaaaca aacaagctgg gagaagcagg aatctgcgct cgggttccgc    180

agatgcagag gttgaggtgg ctgcgggact ggaagtcatc gggcagaggt ctcacagcag    240

ccaaggaacc tggggcccgc tcctcccccc tccaggccat gaggattctg cagttaatcc    300

tgcttgctct ggcaacaggg cttgtagggg gagagaccag gatcatcaag ggggttcgagt   360

gcaagcctca ctcccagccc tggcaggcag ccctgttcga gaagacgcgg ctactctgtg    420

gggcgacgct catcgccccc agatggctcc tgacagcagc ccactgcctc aagccgtggc    480

cgctacatag ttcacctggg gcagcacaac ctccagaagg aggagggctg tgagcagacc    540

cggacagcca ctgagtcctt cccccacccc ggcttcaaca acagcctccc caacaaagac    600

caccgcaatg acatcatgct ggtgaagatg gcatcgccag tctccatcac ctgggctgtg    660

cgacccctca ccctctcctc acgctgtgtc actgctggca ccagctgcct catttccggc    720

tggggcagca cgtccagccc ccagttacgc ctgcctcaca ccttgcgatg cgccaacatc    780

accatcattg agcaccagaa gtgtgagaac gcctaccccg gcaacatcac agacaccatg    840

gtgtgtgcca gcgtgcagga agggggcaag gactcctgcc agggtgactc cgggggccct    900

ctggtctgta accagtctct tcaaggcatt atctcctggg gccaggatcc gtgtgcgatc    960

acccgaaagc ctggtgtcta cacgaaagtc tgcaaatatg tggactggat ccaggagacg   1020

atgaagaaca attagactgg acccacccac cacagcccat caccctccat ttccacttgg   1080

tgtttggttc ctgttcactc tgttaataag aaaccctaag ccaagaccct ctacgaacat   1140

tctttgggcc tcctggacta caggagatgc tgtcacttaa taatcaacct ggggttcgaa   1200

atcagtgaga cctggattca aattctgcct tgaaatattg tgactctggg aatgacaaca   1260

cctggtttgt tctctgttgt atccccagcc ccaaagacag ctcctgccat atatcaagtt   1320

tcaataaata tttct                                                    1335
```

```
<210> SEQ ID NO 7
<211> LENGTH: 1079
<212> TYPE: DNA
<213> ORGANISM: Homo sapiens
<220> FEATURE:
<221> NAME/KEY: misc_feature
```

-continued

```
<222> LOCATION: (268)..(268)
<223> OTHER INFORMATION: n=a, c, g or t
<220> FEATURE:
<221> NAME/KEY: misc_feature
<222> LOCATION: (688)..(688)
<223> OTHER INFORMATION: n=a, c, g or t
<220> FEATURE:
<221> NAME/KEY: misc_feature
<222> LOCATION: (700)..(700)
<223> OTHER INFORMATION: n=a, c, g or t

<400> SEQUENCE: 7

tttttgaaga atgccctgca aggcatcaac tggaatgtgt ttattaccaa acaagacaga     60

agagaaccag ggcctgactt ggcagtggcc ccaggctgca tgggctcagg taggctcaga    120

ccggccccag gagtgggaga gcccagagaa gagggaaaaa gagtagtggc caggaggggt    180

ctggctggga catgccactc tgggccatca gcttctggat ccactcaaag tggtggctga    240

tattggtgta gacaccgggc cgattggncc gaccacagcc cactccccag ctcacgactc    300

caatctgata ccacagtcca ttcttgttac aggccaaggg tccacctgag tcaccgaagc    360

aggcatcctt cccgccttgg gcattgccag cacaaaccat gtctccaaag atgtccttgc    420

ggaaactgta cttgaggaag aggtggttgc acatagagtt gtttatgatg gcgacctgaa    480

cttcctggag ggtgtgggga gatggcagtg cctcatcctc tttgatgtac ccccagccag    540

tcacccagca gtctgtccgg ttctcaaact caaatgtgga ggcctggaga cagatgggct    600

ggatgtgttt agtgtaggtg acaggtgcag acagcttcac caaggcaatg tcatagggtg    660

aattccccag ttagcgaggg ctcagatnga tattcgatan gaagtaacgg gtgtagtagg    720

cctgcaggct ccagaaggat ggcatggaag tcagctggcc aaactggacc atccacccgg    780

agggatcact aaggtcacta taggtttcaa agcagtgcgc cgccgtgagt gcccagcggt    840

ggctgagcag gctcactccg catacgtggg aatcccacag gcgcaggctc ccctgccacg    900

gccaacgccc gagttcggcg tcctctccac ccacgatgcg cgacgtgatg acccgtcggc    960

cgcatggtcc tgataagggc gccgcctcct gcgactccgg cttcctgagt ccagcccgag   1020

ccagcagcag cgccagcagc agcgccccgc gcgcgcccat ggcctcctct cccgcggtg    1079
```

METHOD OF DIAGNOSING, MONITORING, AND STAGING PROSTATE CANCER

CONTINUATION DATA

This application is a division of application 09/700,700, filed on Nov. 20, 2000, now U.S. Pat. No. 6,861,215, which is the 371 national stage application of PCT/US99/10548, filed on May 12, 1999, which claims benefit of 60/086,265, filed on May 21, 1998.

FIELD OF THE INVENTION

This invention relates, in part, to newly developed assays for detecting, diagnosing, monitoring, staging, and prognosticating cancers, particularly prostate cancer.

BACKGROUND OF THE INVENTION

Cancer of the prostate is the most prevalent malignancy in adult males, excluding skin cancer, and is an increasingly prevalent health problem in the United States. In 1996, it was estimated that in the United States, 41,400 deaths would result from this disease, indicating that prostate cancer is second only to lung cancer as the most common cause of death in the same population. If diagnosed and treated early, when the cancer is still confined to the prostate, the chance of cure is significantly higher.

Treatment decisions for an individual are linked to the stage of prostate cancer present in that individual. A common classification of the spread of prostate cancer was developed by the American Urological Association (AUA). The AUA classification divides prostate tumors into four stages, A to D. Stage A, microscopic cancer within prostate, is further subdivided into stages A1 and A2. Sub-stage A1 is a well-differentiated cancer confined to one site within the prostate. Treatment is generally observation, radical prostatectomy, or radiation. Sub-stage A2 is a moderately to poorly differentiated cancer at multiple sites within the prostate. Treatment is radical prostatectomy or radiation. Stage B, palpable lump within the prostate, is further subdivided into stages B1 and B2. In sub-stage B1, the cancer forms a small nodule in one lobe of the prostate. In sub-stage B2, the cancer forms large or multiple nodules, or occurs in both lobes of the prostate. Treatment for both sub-stages B1 and B2 is either radical prostatectomy or radiation. Stage C is a large cancer mass involving most or all of the prostate and is further subdivided into two stages. In sub-stage C1, the cancer forms a continuous mass that may have extended beyond the prostate. In sub-stage C2, the cancer forms a continuous mass that invades the surrounding tissue. Treatment for both these sub-stages is radiation with or without drugs. The fourth stage is metastatic cancer and is also subdivided into two stages. In sub-stage D1, the cancer appears in the lymph nodes of the pelvis. In sub-stage D2, the cancer involves tissues beyond lymph nodes. Treatment for both these sub-stages is systemic drugs to address the cancer as well as pain.

However, current prostate cancer staging methods are limited. As many as 50% of prostate cancers initially staged as A2, B, or C are actually stage D, metastatic. Discovery of metastasis is significant because patients with metastatic cancers have a poorer prognosis and require significantly different therapy than those with localized cancers. The five year survival rates for patients with localized and metastatic prostate cancers are 93% and 29%, respectively.

Accordingly, there is a great need for increasingly sensitive methods for the staging of a cancer in a human to determine whether or not such cancer has metastasized and for monitoring the progress of a cancer in a human.

In the present invention, methods are provided for detecting, diagnosing, monitoring, staging and prognosticating cancers, particularly prostate cancer via seven (7) Prostate Specific Genes (PSG). The seven PSGs refer, among other things, to native proteins expressed by the genes comprising the polynucleotide sequences of any of SEQ ID NO: 1, 2, 3, 4, 5, 6 or 7. In the alternative, what is meant by the seven PSGs as used herein, means the native mRNAs encoded by the genes comprising any of the polynucleotide sequences of SEQ ID NO: 1, 2, 3, 4, 5, 6 or 7 or levels of the genes comprising any of the polynucleotide sequences of SEQ ID NO: 1, 2, 3, 4, 5, 6 or 7.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

SUMMARY OF THE INVENTION

Toward these ends, and others, it is an object of the present invention to provide a method for diagnosing the presence of prostate cancer in a patient which comprises measuring levels of PSG in a sample of cells, tissue or bodily fluid from the patient and comparing the measured levels of PSG with levels of PSG in preferably the same cells, tissue, or bodily fluid type of a control, wherein an increase in the measured PSG levels in the patient versus levels of PSG in the control is associated with prostate cancer.

Another object of the present invention is to provide a method of diagnosing metastatic prostate cancer in a patient which comprises measuring PSG levels in a sample of cells, tissue, or bodily fluid from the patient and comparing the measured PSG levels with levels of PSG in preferably the same cells, tissue, or bodily fluid type of a control, wherein an increase in measured PSG levels in the patient versus levels of PSG in the control is associated with a cancer which has metastasized.

Another object of the present invention is to provide a method of staging prostate cancer in a patient which comprises identifying a patient having prostate cancer, measuring levels of PSG in a sample of cells, tissues, or bodily fluid obtained from the patient, and comparing the measured PSG levels with levels of PSG in preferably the same cells, tissue or bodily fluid type of a control. An increase in measured PSG levels in the patient versus PSG levels in the control can be associated with a cancer which is progressing while a decrease or equivalent level of PSG measured in the patient versus the control can be associated with a cancer which is regressing or in remission.

Another object of the present invention is to provide a method of monitoring prostate cancer in a patient for the onset of metastasis. The method comprises identifying a patient having prostate cancer that is not known to have metastasized, periodically measuring levels of PSG in a sample of cells, tissues, or bodily fluid obtained from the patient, and comparing the measured PSG levels with levels of PSG in preferably the same cells, tissue, or bodily fluid type of a control, wherein an increase in measured PSG levels versus control PSG levels is associated with a cancer which has metastasized.

Yet another object of the present invention is to provide a method of monitoring the change in stage of prostate cancer in a patient which comprises identifying a patient having prostate cancer, periodically measuring levels of PSG in a sample of cells, tissue, or bodily fluid obtained from the patient, and comparing the measured PSG levels with levels of PSG in preferably the same cells, tissues, or bodily fluid type of a control wherein an increase in measured PSG levels versus the control PSG levels is associated with a cancer which is progressing and a decrease in the measured PSG levels versus the control PSG levels is associated with a cancer which is regressing or in remission.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DESCRIPTION OF THE INVENTION

The present invention relates to diagnostic assays and methods, both quantitative and qualitative for detecting, diagnosing, monitoring, staging, and prognosticating cancers by comparing levels of PSG measured in a patient with levels of PSG in a control. What is meant by "levels of PSG" as used herein, means levels of the native protein expressed by the gene comprising the polynucleotide sequence of any of SEQ ID NO: 1, 2, 3, 4, 5, 6 or 7. In the alternative, what is meant by "levels of PSG" as used herein, is levels of the native mRNA encoded by the gene comprising any of the polynucleotide sequence of SEQ ID NO: 1, 2, 3, 4, 5, 6 or 7 or levels of the gene comprising any of the polynucleotide sequence of SEQ ID NO: 1, 2, 3, 4, 5, 6 or 7. Such levels are preferably measured in at least one of cells, tissues and/or bodily fluids, and includes determination of both normal and abnormal levels of PSGs. Thus, for instance, a diagnostic assay in accordance with the invention for diagnosing overexpression of PSG protein compared to control bodily fluids, cells, or tissue samples may be used to diagnose the presence of cancers, including prostate cancer. Any of the seven PSGs may be measured alone in the methods of the invention, all together or in various combinations of the seven PSGs.

By "control" it is meant a human patient without cancer and/or non cancerous samples from the patient, also referred to herein as a normal human control; in the methods for diagnosing or monitoring for metastasis, control may also include samples from a human patient that is determined by reliable methods to have prostate cancer which has not metastasized.

All the methods of the present invention may optionally include measuring the levels of other cancer markers as well as PSG. Other cancer markers, in addition to PSG, useful in the present invention will depend on the cancer being tested and are known to those of skill in the art. For example, simultaneous testing for increases in PSA as well as increases in PSG are also within the scope of the present invention and believed to provide a higher level of assurance that such cancer being tested is metastatic or the onset of metastasis has occurred.

Diagnostic Assays

The present invention provides methods for diagnosing the presence of prostate cancer by analyzing for changes in levels of PSG in cells, tissues or bodily fluids compared with levels of PSG in cells, tissues or bodily fluids of preferably the same type from a normal human control, wherein an increase in levels of PSG in the patient versus the normal human control is associated with the presence of prostate cancer. Without limiting the instant invention, typically, for a quantitative diagnostic assay a positive result indicating the patient being tested has cancer is one in which cells, tissues, or bodily fluid levels of the cancer marker, such as PSG, are at least two times higher, and most preferably are at least five times higher, than in preferably the same cells, tissues, or bodily fluid of a normal human control.

The present invention also provides a method of diagnosing metastatic prostate cancer in a patient having prostate cancer which has not yet metastasized for the onset of metastasis. In the method of the present invention, a human cancer patient suspected of having prostate cancer which may have metastasized (but which was not previously known to have metastasized) is identified. This is accomplished by a variety of means known to those of skill in the art. For example, in the case of prostate cancer, patients are typically diagnosed with prostate cancer following traditional detection methods.

In the present invention, determining the presence of PSG in cells, tissues, or bodily fluid, is particularly useful for discriminating between prostate cancer which has not metastasized and prostate cancer which has metastasized.

Existing techniques have difficulty discriminating between prostate cancer which has metastasized and prostate cancer which has not metastasized and proper treatment selection is often dependent upon such knowledge.

In the present invention, the cancer marker levels measured in such cells, tissue, or bodily fluid are PSGs, and are compared with levels of PSG in preferably the same cells, tissue, or bodily fluid type of a normal human control. That is, if the cancer marker being observed is just PSG in serum, this level is preferably compared with the level of PSG in serum of a normal human patient. An increase in the PSG in the patient versus the normal human control is associated with prostate cancer which has metastasized.

Without limiting the instant invention, typically, for a quantitative diagnostic assay a positive result indicating the cancer in the patient being tested or monitored has metastasized is one in which cells, tissues, or bodily fluid levels of the cancer marker, such as PSG, are at least two times higher, and most preferable are at least five times higher, than in preferably the same cells, tissues, or bodily fluid of a normal patient.

Staging

The invention also provides a method of staging prostate cancer in a human patient.

The method comprises identifying a human patient having such cancer and analyzing a sample of cells, tissues, or bodily fluid from such patient for PSG. Then, the method compares PSG levels in such cells, tissues, or bodily fluid with levels of PSG in preferably the same cells, tissues, or bodily fluid type of a normal human control sample, wherein an increase in PSG levels in the patient versus the normal human control is associated with a cancer which is progressing and a decrease in the levels of PSG is associated with a cancer which is regressing or in remission.

Monitoring

Further provided is a method of monitoring prostate cancer in a human having such cancer for the onset of metastasis. The method comprises identifying a human patient having such cancer that is not known to have metastasized; periodically analyzing a sample of cells, tissues, or bodily fluid from such patient for PSG; and comparing the PSG levels in such cells, tissue, or bodily fluid with levels of PSG in preferably the same cells, tissues, or bodily fluid type of a normal human control sample, wherein an increase in PSG levels in the patient versus the normal human control is associated with a cancer which has metastasized.

Further provided by this invention is a method of monitoring the change in stage of prostate cancer in a human having such cancer. The method comprises identifying a human patient having such cancer; periodically analyzing a sample of cells, tissue, or bodily fluid from such patient for PSG; comparing the PSG levels in such cells, tissue, or bodily fluid with levels of PSG in preferably the same patient.

Monitoring such patient for onset of metastasis is periodic and preferably done on a quarterly basis. However, this may be more or less frequent depending on the cancer, the particular patient, and the stage of the cancer.

Assay Techniques

Assay techniques that can be used to determine levels of gene expression, such as PSG of the present invention, in a sample derived from a host are well-known to those of skill in the art. Such assay methods include radioimmunoassays, reverse transcriptase PCR (RT-PCR) assays, immunohistochemistry assays, in situ hybridization assays, competitive-binding assays, Western Blot analyses and ELISA assays. Among these, ELISAs are frequently preferred to diagnose a gene's expressed protein in biological fluids. An ELISA assay initially comprises preparing an antibody, if not readily available from a commercial source, specific to PSG, preferably a monoclonal antibody. In addition a reporter antibody generally is prepared which binds specifically to PSG. The reporter antibody is attached to a detectable reagent such as radioactive, fluorescent or enzymatic reagent, for example horseradish peroxidase enzyme or alkaline phosphatase.

To carry out the ELISA, antibody specific to PSG is incubated on a solid support, e.g., a polystyrene dish, that binds the antibody. Any free protein binding sites on the dish are then covered by incubating with a non-specific protein such as bovine serum albumin. Next, the sample to be analyzed is incubated in the dish, during which time PSG binds to the specific antibody attached to the polystyrene dish. Unbound sample is washed out with buffer. A reporter antibody specifically directed to PSG and linked to horseradish peroxidase is placed in the dish resulting in binding of the reporter antibody to any monoclonal antibody bound to PSG. Unattached reporter antibody is then washed out. Reagents for peroxidase activity, including a calorimetric substrate are then added to the dish. Immobilized peroxidase, linked to PSG antibodies, produces a colored reaction product. The amount of color developed in a given time period is proportional to the amount of PSG protein present in the sample. Quantitative results typically are obtained by reference to a standard curve.

A competition assay may be employed wherein antibodies specific to PSG attached to a solid support and labeled PSG and a sample derived from the host are passed over the solid support and the amount of label detected attached to the solid support can be correlated to a quantity of PSG in the sample.

Nucleic acid methods may be used to detect PSG mRNA as a marker for prostate cancer. Polymerase chain reaction (PCR) and other nucleic acid methods, such as ligase chain reaction (LCR) and nucleic acid sequence based amplification (NASABA), can be used to detect malignant cells for diagnosis and monitoring of various malignancies. For example, reverse-transcriptase PCR (RT-PCR) is a powerful technique which can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Accordingly, if the mRNA is highly specific for the cell that produces it, RT-PCR can be used to identify the presence of a specific type of cell.

Hybridization to clones or oligonucleotides arrayed on a solid support (i.e., gridding) can be used to both detect the expression of and quantitate the level of expression of that gene. In this approach, a cDNA encoding the PSG gene is fixed to a substrate. The substrate may be of any suitable type including but not limited to glass, nitrocellulose, nylon or plastic. At least a portion of the DNA encoding the PSG gene is attached to the substrate and then incubated with the analyte, which may be RNA or a complementary DNA (cDNA) copy of the RNA, isolated from the tissue of interest.

Hybridization between the substrate bound DNA and the analyte can be detected and quantitated by several means including but not limited to radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

The above tests can be carried out on samples derived from a variety of patients' cells, bodily fluids and/or tissue extracts (homogenates or solubilized tissue) such as from tissue biopsy and autopsy material. Bodily fluids useful in the present invention include blood, urine, saliva, or any other bodily secretion or derivative thereof. Blood can include whole blood, plasma, serum, or any derivative of blood.

EXAMPLES

The present invention is further described by the following examples. These examples are provided solely to illustrate the invention by reference to specific embodiments. These exemplifications, while illustrating certain specific aspects of the invention, do not portray the limitations or circumscribe the scope of the disclosed invention.

Example 1

PSGs

Searches were carried out and PSGs identified using the following Search Tools as part of the LIFESEQ® database available from Incyte Pharmaceuticals, Palo Alto, Calif.:

1. Library Comparison (compares one library to one other library) allows the identification of clones expressed in tumor and absent or expressed at a lower level in normal tissue.
2. Subsetting is similar to library comparison but allows the identification of clones expressed in a pool of libraries and absent or expressed at a lower level in a second pool of libraries.
3. Transcript Imaging lists all of the clones in a single library or a pool of libraries based on abundance. Individual clones can then be examined using Electronic Northerns to determine the tissue sources of their component ESTs.

4. Protein-Function: Incyte has identified subsets of ESTs with a potential protein function based on homologies to known proteins. Some examples in this database include Transcription Factors and Proteases. Some leads were identified by searching in this database for clones whose component ESTs showed disease specificity.

Electronic subtractions, transcript imaging and protein function searches were used to identify clones, whose component ESTs were exclusively or more frequently found in libraries from specific tumors. Individual candidate clones were examined in detail by checking where each EST originated.

TABLE 1

| SEQ ID NO: | Clone ID # | Gene ID # | |
|---|---|---|---|
| 1 | 1550426 | 244673 | Protein Function (Transcription Factors) |
| 2 | 1255804 | 14878 | Subsetting |
| 3 | 1808432 | 255819 | Subsetting |
| 4 | 3930803 | none | Subsetting |
| 5 | 645804 | 235032 | Subsetting |
| 6 | 1862352 | 221558 | Subsetting |
| 7 | 1450626 | 236019 | Subsetting |

Example 2

Measurement of SEQ ID NO:1; Clone ID # 1550426; Gene ID #244673 (pro101)

The example is carried out using standard techniques, which are well known and routine to those of skill in the art, except where otherwise described in detail. Routine molecular biology techniques of the following example are carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989).

Relative Quantitation of Gene Expression

Real-time quantitative PCR with fluorescent Taqman probes is a quantitative detection system utilizing the 5'-3' nuclease activity of Taq DNA polymerase. The method uses an internal fluorescent oligonucleotide probe (Taqman) labeled with a 5' reporter dye and a downstream, 3' quencher dye. During PCR, the 5'-3' nuclease activity of Taq DNA polymerase releases the reporter, whose fluorescence can then be detected by the laser detector of the Model 7700 Sequence Detection System (PE Applied Biosystems, Foster City, Calif., USA).

Amplification of an endogenous control is used to standardize the amount of sample RNA added to the reaction and normalize for Reverse Transcriptase (RT) efficiency. Either cyclophilin, glyceraldehyde-3-phosphate dehydrogenase (GAPDH) or 18S ribosomal RNA (rRNA) is used as this endogenous control. To calculate relative quantitation between all the samples studied, the target RNA levels for one sample are used as the basis for comparative results (calibrator). Quantitation relative to the "calibrator" is obtained using the standard curve method or the comparative method (User Bulletin #2: ABI PRISM 7700 Sequence Detection System).

To evaluate the tissue distribution, and the level of pro101 (SEQ ID NO:1) in normal and tumor tissue, total RNA was extracted from tumor and matched normal adjacent tissues and from unmatched tumor and normal tissues. Subsequently, first strand cDNA was prepared with reverse transcriptase and the polymerase chain reaction carried out using primers and Taqman probe specific to pro101 (SEQ ID NO:1). The results were obtained using the ABI PRISM 7700 Sequence Detector. The absolute numbers are relative levels of expression of pro101 (SEQ ID NO:1) compared to the calibrator.

The absolute numbers are depicted in the following Table 2 as relative levels of expression in 12 normal tissues of pro101 (SEQ ID NO:1) compared to kidney (calibrator). These RNA samples were generated by pooling samples from a particular tissue from different individuals.

TABLE 2

Relative levels of pro101 Expression in Pooled Samples

| Tissue | NORMAL |
|---|---|
| Brain | 1.2 |
| Heart | 2 |
| Kidney | 1 |
| Liver | 7.2 |
| Lung | 48.2 |
| Mammary | 2.5 |
| Prostate | 1418.4 |
| Spleen | 1.6 |
| Small | 1.9 |
| Testis | 57.3 |
| Thymus | 1.3 |
| Uterus | 7.6 |

The relative levels of expression in Table 2 show that for the PSG pro101 (SEQ ID NO:1) mRNA expression is more than 20 fold higher in the pool of normal prostate compared with the other 11 normal tissue pools analyzed. These results demonstrate that mRNA expression of the PSG is highly specific for prostate.

The tissues shown in Table 2 correspond to pools of samples from different individuals. The tissues shown in the following Table 3 were obtained from individuals and are not pooled. Hence the values for mRNA expression levels shown in Table 2 cannot be directly compared to the values shown in Table 3.

The absolute numbers in Table 3 are relative levels of expression of pro101 (SEQ ID NO:1) compared to kidney (calibrator), in 60 pairs of matching samples. Each matching pair contains the cancer sample for a particular tissue and the normal adjacent sample for that same tissue from the same individual. The results from 3 unmatched ovary tumor, 3 unmatched normal ovary, 1 unmatched mammary tumor and 1 unmatched normal mammary gland are also shown.

TABLE 3

Relative Levels of pro101 Expression in Individual Samples

| TISSUE | CANCER | MATCHING | UNMATCHED |
|---|---|---|---|
| Prostate 1 | 103.9 | 0 | |
| Prostate 2 | 2219 | 84.2 | |
| Prostate 3 | 5048.2 | 3623.6 | |
| Prostate 4 | 11052.3 | 2029.4 | |
| Prostate 5 | 229.1 | 41.1 | |
| Prostate 6 | 57.9 | 25.3 | |
| Prostate 7 | 58.5 | 57.069 | |
| Prostate 8 | 1074.6 | 610.8 | |
| Prostate 9 | 32.7 | 79.3 | |
| Prostate 10 | 15.8 | 2.09 | |
| Prostate 11 | 436.4 | 438 | |
| Prostate 12 | 49.5 | 59.3 | |
| Prostate 13 | 128 | 56 | |
| Bladder 1 | 0 | 0 | |
| Bladder 2 | 0 | 0 | |
| Bladder 3 | 0.7 | 0 | |
| Colon 1 | 0 | 0 | |
| Colon 2 | 0 | 0 | |
| Colon 3 | 0 | 0 | |
| Colon 4 | 3.3 | 1.9 | |
| Colon 5 | 0.1 | 0.8 | |

TABLE 3-continued

| Relative Levels of pro101 Expression in Individual Samples | | | |
|---|---|---|---|
| TISSUE | CANCER | MATCHING | UNMATCHED |
| Colon 6 | 0 | 0 | |
| Lung 1 | 0 | 0 | |
| Lung 2 | 0.5 | 1.6 | |
| Lung 3 | 1.4 | 2.1 | |
| Lung 4 | 0 | 0 | |
| Lung 5 | 0 | 0 | |
| Kidney 1 | 0 | 0 | |
| Kidney 2 | 0 | 0 | |
| Kidney 3 | 0 | 0 | |
| Kidney 4 | 0 | 0 | |
| Liver 1 | 1.5 | 5.7 | |
| Liver 2 | 26.9 | 7.9 | |
| Liver 3 | 0 | 0 | |
| Pancreas 1 | 0.9 | 0.9 | |
| Pancreas 2 | 3 | 0 | |
| Pancreas 3 | 0 | 0 | |
| Pancreas 4 | 0 | 0 | |
| Pancreas 5 | 0 | 0 | |
| Stomach 1 | 0 | 0 | |
| Stomach 2 | 0 | 0 | |
| Stomach 3 | 0 | 0 | |
| Stomach 4 | 0 | 0 | |
| Stomach 5 | 0 | 0 | |
| Sm Int 1 | 0 | 0 | |
| Sm Int 2 | 0 | 0 | |
| Testis 1 | 0 | 0 | |
| Mammary 1 | 4 | 0 | |
| Mammary 2 | 5.6 | 0 | |
| Mammary 3 | 0.5 | 0 | |
| Mammary 4 | 0.4 | 0 | |
| Mammary 5 | 0.5 | | |
| Mammary 6 | | | 0 |
| Endo 1 | 1.6 | 7.6 | |
| Endo 2 | 0 | 0 | |
| Endo 3 | 0 | 0 | |
| Endo 4 | 0.3 | 0.2 | |
| Endo 5 | 5.8 | 5 | |
| Uterus 1 | 0 | 0 | |
| Uterus 2 | 0 | 0 | |
| Uterus 3 | 0 | 0 | |
| Uterus 4 | 2.2 | 2.6 | |
| Ovary 1 | 1.4 | | |
| Ovary 2 | | | 11.6 |
| Ovary 3 | 1.5 | | |
| Ovary 4 | | | 22.9 |
| Ovary 5 | 0 | | |
| Ovary 6 | | | 1.8 |

Among 128 samples in Table 3 representing 14 different tissues, the higher levels of expression are consistently in prostate tissues. These results confirm the tissue specificity results obtained with normal samples shown in Table 2. Table 2 and Table 3 represent a combined total of 140 samples in 18 human tissue types. Sixty-eight samples representing 13 different tissue types excluding prostate had no detected pro101 mRNA (Table 3). In 4 tissues (stomach small intestine kidney and testis) no pro101 (SEQ ID NO:1) mRNA was detected for any sample tested from individuals (Table 3). Expression of this PSG was detected in testis in the pooled normal sample (Table 3). The median expression in prostate cancer samples in Table 3 is 166.5 units. Excluding Ovary 4 (Normal), only 1 sample in Table 3, Liver 2 (Cancer), is greater than 10% of this value.

Comparisons of the level of mRNA expression in prostate tumor samples and the normal adjacent tissue from the same individuals are also shown in Table 3. The PSG pro101 (SEQ ID NO:1) is expressed at higher levels in 9 of 13 (69%) prostate cancer tissues (Prostate 1, 2, 3, 4, 5, 6, 8, 10 and 13) compared with the corresponding normal adjacent tissue. The level of expression of this PSG is lower in prostate tumor compared to normal adjacent tissue in two samples (Prostate 9 and 12). Equivalent levels of expression were detected in two matched samples (Prostate 7 and 11). Previous mRNA expression analysis for genes coding for the diagnostic markers PSA and PLA2 showed higher expression of the mRNA in 40% to 80% of the tumor samples compared to matching normal adjacent tissue. Higher expression ins the tumor sample compared to the corresponding normal adjacent tissue is observed for Bladder 3, Colon 4, Liver 2, Pancreas 2, Endometrium 5 and. Mammary 1, 2 and 3. Higher expression in the normal adjacent samples is observed for Colon 5, Lung 2, Lung 3, Liver 1, Endometrium 1 and Uterus 4. However, the levels detected are in most cases comparable amongst the different tissues and low compared to levels found in most prostate tissues.

The high level of tissue specificity, plus the mRNA overexpression in 9 of 13 of the prostate tumor samples tested compared to the normal adjacent tissues are believed to make the PSG, pro101 (SEQ ID NO:1) a good diagnostic marker for detection of prostate cancer using mRNA.

What is claimed is:

1. A method for detecting the presence of prostate cancer in a patient comprising:

(a) measuring levels of SEQ ID NO:7 in a sample of, prostate tissue or bodily fluid obtained from the patient; and (b) comparing the measured levels of SEQ ID NO:7 with levels of SEQ ID NO:7 in a sample of prostate tissue or bodily fluid from a non-cancerous control, wherein an increase in measured levels of SEQ ID NO:7 in the patient versus the SEQ ID NO:7 levels in the control is associated with the presence of prostate cancer.

2. The method of claim 1, wherein SEQ ID NO:7 is a mRNA.

3. The method of claim 1, wherein the sample is prostate tissue.

4. The method of claim 1, wherein the sample is bodily fluid.

5. The method of claim 1, wherein the bodily fluid is selected from the group comprising blood, urine and saliva.

6. The method of claim 5, wherein blood comprises whole blood, plasma or serum.

7. The method of claim 1, wherein levels of SEQ ID NO:7 are measured by reverse transcriptase PCR (RT-PCR), in situ hybridization or oligonucleotide array.

* * * * *